(12) United States Patent
Hermeling et al.

(10) Patent No.: US 7,772,420 B2
(45) Date of Patent: Aug. 10, 2010

(54) (METH)ACRYLIC ESTERS OF MONOALKOXYLATED POLYOLS, AND PRODUCTION THEREOF

(75) Inventors: Dieter Hermeling, Böhl-Iggelheim (DE); Thomas Daniel, Waldsee (DE); Mark Elliott, Ludwigshafen (GB); Ulrich Riegel, Landstuhl (DE); Frank Dietsche, Schriesheim (DE); Reinhold Schwalm, Wachenheim (DE)

(73) Assignee: BASF Aktiengesellschaft

( * ) Notice: Subject to any disclaimer, the term of this patent is extended or adjusted under 35 U.S.C. 154(b) by 417 days.

(21) Appl. No.: 10/562,239

(22) PCT Filed: Jun. 30, 2004

(86) PCT No.: PCT/EP2004/007078

§ 371 (c)(1),
(2), (4) Date: Feb. 10, 2006

(87) PCT Pub. No.: WO2005/005514

PCT Pub. Date: Jan. 20, 2005

(65) Prior Publication Data

US 2006/0155057 A1    Jul. 13, 2006

(30) Foreign Application Priority Data

Jul. 10, 2003    (DE)    ................. 103 31 450

(51) Int. Cl.
C07C 69/33    (2006.01)
C07C 69/54    (2006.01)
C08G 63/52    (2006.01)
C08G 63/02    (2006.01)
C08G 18/62    (2006.01)

(52) U.S. Cl. ............. 560/224; 560/205; 528/271; 528/272; 528/361; 524/916; 525/451

(58) Field of Classification Search .......... 524/916; 525/418, 451; 528/271, 300, 272, 361; 560/205, 560/224

See application file for complete search history.

(56) References Cited

U.S. PATENT DOCUMENTS

| | | | | |
|---|---|---|---|---|
| 4,065,598 A * | 12/1977 | Takahashi et al. | ............ | 428/394 |
| 4,581,470 A * | 4/1986 | Hoy et al. | ................... | 560/189 |
| 4,873,299 A | 10/1989 | Nowakowsky et al. | | |
| 5,335,726 A * | 8/1994 | Rodrigues | ................... | 166/295 |
| 5,574,121 A * | 11/1996 | Irie et al. | ............... | 526/318.44 |
| 5,821,383 A * | 10/1998 | Haussling et al. | ........... | 560/205 |
| 6,395,830 B1 | 5/2002 | Jonas et al. | | |
| 6,818,791 B2 * | 11/2004 | Martin et al. | ............... | 560/205 |
| 7,250,481 B2 * | 7/2007 | Jaworek et al. | ............. | 526/321 |
| 2004/0077796 A1 * | 4/2004 | Daniel et al. | ................ | 525/360 |
| 2005/0165208 A1 * | 7/2005 | Popp et al. | .................. | 528/300 |

FOREIGN PATENT DOCUMENTS

| | | |
|---|---|---|
| DE | 29 13 218 A1 | 10/1980 |
| EP | 238 050 | 9/1987 |
| EP | 322 110 | 6/1989 |
| EP | 490368 A1 * | 6/1992 |
| JP | 62007711 A * | 1/1987 |
| JP | 06 145 341 | 5/1994 |
| WO | WO 93/21237 | 10/1993 |
| WO | WO 98/47951 | 10/1998 |
| WO | WO 01/41818 A1 | 6/2001 |
| WO | WO 01/56625 A2 | 8/2001 |
| WO | WO 03104301 A1 * | 12/2003 |

OTHER PUBLICATIONS

International Search Report dated Nov. 11, 2004 for PCT/EP2004/007078 filed Jun. 30, 2004.

* cited by examiner

*Primary Examiner*—Mark Eashoo
*Assistant Examiner*—Michael Pepitone
(74) *Attorney, Agent, or Firm*—Marshall, Gerstein & Borun LLP

(57) ABSTRACT

Disclosed are novel (meth)acrylic esters of monoalkoxylated polyols, a process for their preparation and their use for preparing crosslinked swellable hydrogel-forming polymers and crosslinked swellable hydrogel-forming polymers.

15 Claims, No Drawings

(METH)ACRYLIC ESTERS OF MONOALKOXYLATED POLYOLS, AND PRODUCTION THEREOF

CROSS-REFERENCE TO RELATED APPLICATIONS

This is the U.S. national phase application of International Application No. PCT/EP2004/007078, filed Jun. 30, 2004, which claims the benefit of German patent application No. 103 31 450.4, filed Jul. 10, 2003.

The present invention relates to novel (meth)acrylic esters of monoalkoxylated polyols, a process for their preparation and also their use for preparing crosslinked swellable hydrogel-forming polymers and crosslinked swellable hydrogel-forming polymers.

The terms (meth)acrylic acid and (meth)acrylic ester represent methacrylic acid and acrylic acid on the one hand and methacrylic ester and acrylic ester on the other.

Swellable hydrogel-forming polymers, known as superabsorbent polymers or SAPs, are known from the prior art.

Hydrophilic high-swell hydrogels are in particular polymers of (co)polymerized hydrophilic monomers, graft (co)polymers of one or more hydrophilic monomers on a suitable grafting base, crosslinked cellulose or starch ethers, crosslinked carboxymethylcellulose, partially crosslinked polyalkylene oxide or natural products which swell in aqueous fluids, for example guar derivatives. Such hydrogels are used as products which absorb aqueous solutions to manufacture diapers, tampons, sanitary napkins and other hygiene articles, but also as water-retaining agents in market gardening.

Good transportation properties are possessed for example by hydrogels having high gel strength in the swollen state. Gels lacking in strength are deformable under an applied pressure, for example pressure due to bodyweight, and clog the pores in the SAP/cellulose fiber absorbent and so prevent continued absorption of fluid. Enhanced gel strength is generally obtained through a higher degree of crosslinking, although this reduces retention performance of the product. An elegant way to enhance gel strength is surface postcrosslinking. In this process, dried superabsorbents having an average crosslink density are subjected to an additional crosslinking step. Surface postcrosslinking increases the crosslink density in the surface shell of the superabsorbent particle, whereby the absorbency under load is raised to a higher level. Whereas the absorption capacity decreases in the superabsorbent particle shell, the core has an improved absorption capacity (compared to the shell) owing to the presence of mobile polymer chains, so that shell construction ensures improved fluid transmission without occurrence of the gel blocking effect. It is perfectly desirable for the total capacity of the superabsorbent to be exhausted not spontaneously but with time delay. Since the hygiene article is generally repeatedly insulted with urine, the absorption capacity of the superabsorbent should sensibly not be exhausted after the first disposition.

EP-A-0 238 050 discloses (as possible internal crosslinkers for superabsorbents) trimethylolpropane triacrylate, at least doubly acrylated or methacrylated glycerol, doubly or triply acrylated or methacrylated addition products of ethylene oxide and propylene oxide with trimethylolpropane.

Sartomer (Exton, Pa., USA), for example, sells under the indicated trade names trimethylolpropane triacrylate (SR 351), triply monoethoxylated trimethylolpropane triacrylate (SR 454), triply diethoxylated trimethylolpropane triacrylate (SR 499), triply triethoxylated trimethylolpropane triacrylate (SR 502), triply pentaethoxylated trimethylolpropane triacrylate (SR 9035) and altogether 20-tuply ethoxylated trimethylolpropane triacrylate (SR 415). Propoxylated trimethylolpropane triacrylates are obtainable under the trade names SR 492 (triply monopropoxylated trimethylolpropane triacrylate) and CD 501 (triply dipropoxylated trimethylolpropane triacrylate).

WO 93/21237 discloses (meth)acrylates of alkoxylated polyhydric $C_2$-$C_{10}$ hydrocarbons that are useful as crosslinkers. The trimethylolpropane crosslinkers used correspond to SR 351, SR 454, SR 502, SR 9035 and SR 415 from Sartomer. These crosslinkers have 0, 3, 9, 15 or 20 ethylene oxide units per molecule of trimethylolpropane triacrylate. WO 93/21237 says it is advantageous to have 2 to 7 ethylene oxide units per chain in the trimethylolpropane triacrylate and especially 4 to 6 EO units per chain in the trimethylolpropane triacrylate.

Ethoxylated trimethylolpropane tri(meth)acrylates are again and again mentioned as internal crosslinkers in the patent literature, although only the trimethylolpropane triacrylate derivatives commercially available from Sartomer are used, for example triply monoethoxylated trimethylolpropane triacrylate in WO 98/47951, Sartomer® SR 9035 as a so-called highly ethoxylated trimethylolpropane triacrylate (HeTMPTA) in WO 01/41818 and Sartomer® SR 9035 and Sartomer® SR 492 in WO 01/56625.

It is an object of the present invention to provide further compounds useful as free-radical crosslinkers for superabsorbents.

It is a further object of the present invention to provide crosslinked water-swellable polymers having a balanced property profile with regard to absorption capacity, gel strength, takeup rate and extractables that are also advantageously producible in a continuous process.

Unless otherwise mentioned, crosslinking as used herein is to be understood as meaning gel crosslinking, internal crosslinking or cross-linking of linear or lightly crosslinked polymer. This crosslinking can take place via free-radical or cationic polymerization mechanisms or other mechanisms, for example Michael addition, esterification or transesterification mechanisms, but is preferably effected by free-radical polymerization.

Crosslinked swellable hydrogel-forming polymers are preferably capable of absorbing at least 10 times their own weight and preferably 20 times their own weight, based on the polymer used, of 0.9% by weight sodium chloride solution. This absorption is preferably achieved even under a pressure of 0.7 psi for example.

We have found that the aforementioned objects are achieved by using novel crosslinkers.

The present invention accordingly provides (meth)acrylic esters of monoalkoxylated polyols of the general formula I

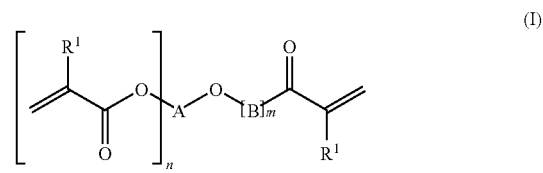

where
$R^1$ is hydrogen or methyl,
n is an integer from 2 to 5,
m is an integer from 1 to 100, A is $C_3$ to $C_{20}$ alk(n+1)yl or $C_3$ to $C_{20}$ heteroalk(n+1)yl, and
B represents identical or different radicals selected from the group consisting of

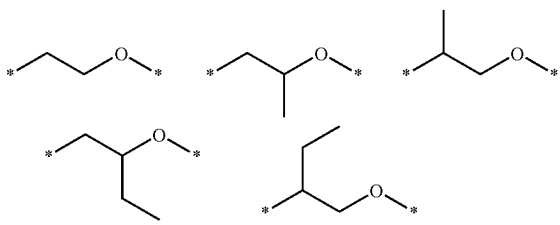

where * identifies the positions of attachment.

Preference is given to (meth)acrylic esters of monoalkoxylated polyols of the general formula I where
$R^1$ is hydrogen or methyl,
n 2 or 3,
m is an integer from 2 to 50,
A $C_3$ to $C_{10}$ alk(n+1)yl, and
B represents identical or different radicals selected from the group consisting of

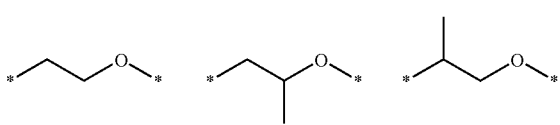

where * identifies the positions of attachment.

Particular preference is given to (meth)acrylic esters of monoalkoxylated polyols of the general formula I where
$R^1$ is hydrogen or methyl,
n is 2,
m is an integer from 3 to 30,
A is $C_3$ to $C_6$ alk(n+1)yl, and
B is

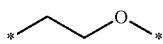

where * identifies the positions of attachment.

Most preference is given to (meth)acrylic esters of monoalkoxylated glycerols. The inventive (meth)acrylic esters of monoalkoxylated polyols are preparable for example from an alcohol of the general formula II

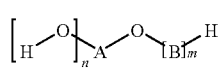

(II)

where
m, n, A and B are each as defined above.

By reaction with (meth)acrylic acid, transesterification with a (meth)acrylic ester and also by acidolysis with (meth) acryloyl chloride or (meth)acrylic anhydride. The reaction with (meth)acrylic acid is preferred.

The preparation of (meth)acrylic esters by acid-catalyzed esterification of (meth)acrylic acid with alkanols is common knowledge, see for example Ullmann's Encyclopedia of Industrial Chemistry, Vol. A1, pages 162 to 169, VCH 1985. The formation of the ester from (meth)acrylic acid and alkanol is known to be based on an equilibrium reaction. To obtain commercially viable conversions, the general approach is to use one starting material in excess and/or remove the resulting water of esterification from the equilibrium. To speed and facilitate water removal, it is customary to add an organic solvent which is not miscible with water and/or forms an azeotrope with water. Solvents used are frequently aliphatic, cycloaliphatic and/or aromatic hydrocarbons, such as pentanes, hexanes, heptanes, cyclohexane or toluene, see for example DE-A-20 50 678, DE-A-29 13 218, U.S. Pat. No. 4,053,504, U.S. Pat. No. 2,917,538 and EP-A-0 618 187.

Useful alcohols include monoalkoxylated polyols which are obtainable by reaction of a partially protected polyol with at least one alkylene oxide.

Preferably, the protective groups are only removed immediately prior to the esterification. Useful catalysts for the hydrolysis include the abovementioned esterification catalysts, preferably sulfuric acid.

Useful partially protected polyols include for example methylideneglycerol(4-hydroxymethyl-1,3-dioxolane), ethylideneglycerol(4-hydroxymethyl-2-methyl-1,3-dioxolane), isopropylidenglycerol(4-hydroxymethyl-2,2-dimethyl-1,3-dioxolane), sec-butylideneglycerol(2-ethyl-4-hydroxymethyl-2-methyl-1,3-dioxolane), glycerol 1,2-divinyl ether, glycerol 1,3-divinyl ether, methylidentrimethylolpropane(5-ethyl-5-hydroxymethyl-1,3-dioxane), ethylidenetrimethylolpropane(5-ethyl-5-hydroxymethyl-2-methyl-1,3-dioxane), isopropylidenetrimethylolpropane(5-ethyl-5-hydroxymethyl-2,2-dimethyl-1,3-dioxane), sec-butylidenetrimethylolpropane(2,5-diethyl-5-hydroxymethyl-2-methyl-1,3-dioxane), trimethylolpropane divinyl ether and pentaerythritol trivinyl ether. Preference is given to isopropyleneglycerol and isopropylidenetrimethylolpropane and most preference is given to isopropylidenetrimethylolpropane.

Useful alkylene oxides include for example ethylene oxide, propylene oxide and/or butylene oxide.

The alkylene oxide chain may preferably be composed of ethylene oxide, propylene oxide and/or butylene oxide units. Such a chain can be composed of one species of an alkylene oxide or of a mixture of alkylene oxides. When a mixture is used, the different alkylene oxide units may be present randomly or as a block or blocks of individual species. The alkylene oxide is preferably ethylene oxide, propylene oxide or a mixture thereof, more preferably ethylene oxide or a mixture of ethylene oxide and propylene oxide and most preferably ethylene oxide.

The preferred number of alkylene oxide units in the chain is from 1 to 100, preferably from 2 to 50, more preferably from 3 to 30 and most preferably from 4 to 20.

The stated degrees of alkoxylation each relate to the average degree of alkoxylation.

The reaction of partially protected polyols with an alkylene oxide is known per se to one skilled in the art. Possible ways of conducting the reaction may be found in Houben-Weyl, Methoden der Organischen Chemie, 4th edition, 1963, Thieme Verlag Stuttgart, volume 14/2, pages 440 to 444.

When mixed-monoalkoxylated polyols are used, the different alkoxy groups present therein may be in a molar ratio to each other which is for example 0.05-20:1, preferably 0.1-10:1 and more preferably 0.2-5:1.

The viscosity of the monoalkoxylated polyols which can be used according to the present invention is not subject to any particular requirements bar that they should be readily pumpable to about 80° C., preferably they should have a viscosity below 1000 mPas, preferably below 800 mPas and most preferably below 500 mPas.

One skilled in the art would know how to prepare partially protected polyols. By way of example, DE-A-1 96 47 395 describes the synthesis of isopropylideneglycerol, sec-butylideneglycerol and isopropylidenetrimethylolpropane.

The acidic esterification catalyst used is preferably sulfuric acid. Other useful esterification catalysts include organic sulfonic acids, for example methanesulfonic acid, benzenesulfonic acid, p-toluenesulfonic acid or dodecylbenzenesulfonic acid and/or acidic ion exchangers. The esterification catalyst is generally used in an amount from 0.1 to 10% by weight and preferably 0.5 to 5% by weight, based on (meth) acrylic acid and monoalkoxylated polyols.

Useful polymerization inhibitors include for example phenols such as alkylphenols, for example o-, m- or p-cresol (methylphenol), 2-tert-butyl-4-methylphenol, 2,6-di-tert-butyl-4-methylphenol, 2-tert-butylphenol, 4-tert-butylphenol, 2,4-di-tert-butylphenol, hydroquinone, pyrocatechol(1,2-dihydroxybenzene), aminophenols, for example para-aminophenol, nitrosophenols, for example para-nitrosophenol, p-nitroso-o-cresol, alkoxyphenols, for example 2-methoxyphenol (guaiacol, pyrocatechol monomethyl ether), 2-ethoxyphenol, 2-isopropoxyphenol, 4-methoxyphenol(hydroquinone monomethyl ether), quinones and hydroquinones, for example hydroquinone or hydroquinone monomethyl ether, 2,5-di-tert-butylhydroquinone, benzoquinone, N-oxyls, for example 4-hydroxy-2,2,6,6-tetramethylpiperidine N-oxyl, 4-oxo-2,2,6,6-tetramethylpiperidine N-oxyl, 4-acetoxy-2,2,6,6-tetramethylpiperidine N-oxyl, 2,2,6,6-tetramethylpiperidine N-oxyl, aromatic amines, for example phenylenediamines, N,N-diphenylamine, N-nitrosodiphenylamine, nitrosodiethylaniline, N,N'-dialkylpara-phenylenediamine, wherein the alkyl radicals may be identical or different and may each independently consist of 1 to 4 carbon atoms and be straight-chain or branched, for example N,N'-diisobutyl-p-phenylenediamine, N,N'-diisopropyl-p-phenylenediamine, hydroxylamines, for example N,N-diethylhydroxylamine, urea derivatives, for example urea or thiourea, phosphorus compounds, for example, triphenylphosphine, triphenyl phosphite, hypophosphorous acid or triethyl phosphite, sulfur compounds, for example diphenyl sulfide, phenothiazine or metal salts, for example copper chloride, copper dithiocarbamate, copper sulfate, copper salicylate, copper acetate, manganese chloride, manganese dithiocarbamate, manganese sulfate, manganese salicylate, manganese acetate, cerium chloride, cerium dithiocarbamate, cerium sulfate, cerium salicylate, cerium acetate, nickel chloride, nickel dithiocarbamate, nickel sulfate, nickel salicylate, nickel acetate, chromium chloride, chromium dithiocarbamate, chromium sulfate, chromium salicylate, chromium acetate or mixtures thereof.

Preference is given to the phenols and quinones mentioned and particular preference is given to hydroquinone, hydroquinone monomethyl ether, 2-tert-butyl-4-methylphenol, 2,6-di-tert-butyl-4-methylphenol, 2,4-di-tert-butylphenol, triphenyl phosphite, hypophosphorous acid, $CuCl_2$ and guaiacol.

Particular preference is given to hydroquinone monomethyl ether, hydroquinone and alkylphenols, optionally in combination with triphenyl phosphite and/or hypophosphorous acid.

Stabilization may be further augmented by the presence of an oxygen-containing gas, preferably air or a mixture of air and nitrogen (lean air). The oxygen-containing gas more preferably contains less than 10% by volume of oxygen and most preferably from 4 to 6% by volume of oxygen.

Among the recited stabilizers, preference is given to those which are aerobic, i.e., those which required the presence of oxygen to fully develop their inhibiting effect.

The esterification may of course also be carried out using solvents, particularly solvents which are suitable for azeotropic removal of water, especially aliphatic, cycloaliphatic and aromatic hydrocarbons or mixtures thereof.

Preference is given to n-pentane, n-hexane, n-heptane, cyclohexane, methylcyclohexane, benzene, toluene or xylene. Particular preference is given to cyclohexane, methylcyclohexane and toluene.

The esterification may in general be carried out as follows:

The esterification apparatus comprises for example a stirred reactor, preferably a reactor with circulatory evaporator and an added distillation unit.

The reactor may be for example a reactor with jacketed heating and/or internal heating coils. Preference is given to using a reactor having an external heat exchanger and natural or forced circulation, i.e., through use of a pump, more preferably natural circulation where circulation is accomplished without mechanical aids.

It will be appreciated that the reaction can also be carried out in a plurality of reaction zones, for example a reactor battery of two to four and preferably two or three reactors.

Suitable circulatory evaporators are known to one skilled in the art and are described for example in R. Billet, Verdampfertechnik, HTB-Verlag, Bibliographisches Institut Mannheim, 1965, page 53. Examples of circulatory evaporators are tube-bundle heat exchangers, plate-type heat exchangers, etc.

It will be appreciated that the circulatory system may also include a plurality of heat exchangers.

To hydrolyze partially protected monoalkoxylated polyols, the partially protected monoalkoxylated polyol, the hydrolsis catalyst and water are introduced into the reactor. The reaction mixture is heated to the boil using the circulatory evaporator and the protective group which has been detached by hydrolysis, acetone for example, is distilled off if desired.

To carry out the esterification, the materials used are introduced into the reactor. The reaction mixture is heated to the boil with the aid of the circulatory evaporator and the water formed in the course of the esterification is distilled off as an azeotrope with the organic solvent. This is done via a distillation unit (on top of the reactor) which comprises a distillation column and a condenser.

Preferably, hydrolysis and esterification are carried out in succession in one reactor without intervening purification.

The distillation unit is of conventional design. It may be a simple distillation unit which if appropriate is equipped with a splash guard or it may be a rectification column. Suitable column internals include in principle all common internals, for example trays, structured packings and/or dumped packings. Preferred trays include bubble-cap trays, sieve trays, valve trays, Thormann trays and/or dual-flow trays, while preferred dumped packings are those of rings, coils, saddles or braids.

In general, from 5 to 20 theoretical plates are sufficient.

The condenser is likewise of traditional design, for example it may be a tube or plate heat exchanger. They are preferably operated using water or brines.

The (meth)acrylic acid and the monoalkoxylated polyol are generally used in the esterification in a molar excess as indicated above based on the hydroxyl groups of the alcohol. The excess used can be up to about 1000:1, if desired.

Useful esterification catalysts include those recited above.

The polymerization inhibitor (mixture) is generally used in a total amount from 0.01 to 1% by weight, based on the transesterification mixture, preferably from 0.02 to 0.8% by weight, more preferably from 0.05 to 0.5% by weight.

The polymerization inhibitor (mixture) can be used for example as an alcoholic solution or as a solution in a reactant or product.

Stabilization may be further augmented by the presence of an oxygen-containing gas, preferably air or a mixture of air and nitrogen (lean air).

This oxygen-containing gas is preferably metered into the bottom region of a column and/or into a circulatory evaporator and/or passed through and/or over the reaction mixture.

The water of reaction can be distilled off during or after the esterification, in which case this operation can be augmented by a solvent which forms an azeotrope with water.

Useful solvents for azeotropic removal of the water, if desired, include the hydrocarbons recited above.

The esterification is preferably carried out in the presence of an excess of (meth)acrylic acid.

When the water in the reaction mixture is not removed via an azeotrope-forming solvent, it may be removed by stripping with an inert gas, preferably an oxygen-containing gas and more preferably air or lean air.

The reaction temperature for the esterification is generally in the range from 40 to 160° C., preferably in the range from 60 to 140° C. and more preferably in the range from 80 to 120° C. The temperature may remain constant or rise in the course of the reaction and preferably it is raised in the course of the reaction. In this case, the final temperature of the esterification is 5-30° C. higher than the initial temperature. The temperature for the esterification can be controlled by varying the solvent concentration in the reaction mixture or by varying the reaction pressure.

Preferably, the azeotrope of the water formed and the organic solvent is removed via the distillation column and then condensed in the condenser, the condensate separating into an aqueous phase and an organic phase. The aqueous phase is partly or wholly removed from the system or may be forwarded for further processing to recover the (meth)acrylic acid present therein. The organic phase constitutes the reflux and it is wholly or partly passed into the circuit between reactor and circulatory evaporator. Preferably, at least 10% by weight of the reflux is passed into the circuit. The reflux may be injected into the pipe which leads from the reactor to the circulatory evaporator and which forms the feed line to the circulatory evaporator, or alternatively into the feed region of the circulatory evaporator. After passing through the circulatory evaporator, the reaction mixture is returned into the reactor.

The reflux, as described in DE-A-199 41 136, may be used for controlling the temperature in the esterification.

The esterification can be carried out at atmospheric pressure, at superatmospheric pressure or at reduced pressure and is preferably carried out at atmospheric pressure or reduced pressure and more preferably at a reaction pressure in the range from 200 to 1013 mbar.

The reaction time is generally in the range from 2 to 20 hours, preferably in the range from 4 to 15 and more preferably in the range from 7 to 12 hours.

The order in which the individual reaction components are added is not critical. All the components can be introduced as a mixed initial charge and subsequently heated, or one or more components can be omitted from or only partly included in the initial charge and added only after the initial charge has been heated up.

When the esterification is carried out in a reactor equipped with a natural-circulation evaporator, it will be advantageous for the lower-boiling reaction components to be at least partly included in the initial charge.

The (meth)acrylic acid which can be used is not restricted in its composition and may comprise for example the following components:

| | |
|---|---|
| (Meth)acrylic acid | 90–99.9% by weight |
| Acetic acid | 0.05–3% by weight |
| Propionic acid | 0.01–1% by weight |
| Diacrylic acid | 0.01–5% by weight |
| Water | 0.05–5% by weight |
| Carbonylics | 0.01–0.3% by weight |
| Inhibitors | 0.01–0.1% by weight |
| Maleic acid or anhydride | 0.001–0.5% by weight |

The crude (meth)acrylic acid used is generally stabilized with 200-600 ppm of phenothiazine or other stabilizers in amounts which permit comparable stabilization. Carbonylics here refers for example to acetone and lower aldehydes, for example formaldehyde, acetaldehyde, crotonaldehyde, acrolein, 2-furfural, 3-furfural and benzaldehyde.

Crude (meth)acrylic acid here refers to the (meth)acrylic acid mixture which is obtained after absorption of the reaction gases of the propane/propene/acrolein or isobutane/isobutene/methacrolein oxidation in an absorbent and subsequent removal of the absorbent, or which is obtained by fractional condensation of the reaction gases.

It is obviously also possible to use pure (meth)acrylic acid, which is substantially free of aldehydic, other carbonylic and high-boiling components, having for example a purity of more than 99.5% by weight.

The aqueous phase, distilled off during the esterification, of the condensate removed via the added column (if present) may generally contain 0.1-10% by weight of (meth)acrylic acid, and is separated off and removed from the system. The (meth)acrylic acid it contains may preferably be extracted with an extractant, preferably with any solvent used in the esterification, for example with cyclohexane, at from 10 to 40° C. and a ratio of 1:5-30 and preferably 1:10-20 for aqueous phase to extractant, and returned into the esterification.

Circulation may be further supported by passing an inert gas, preferably an oxygen-containing gas, more preferably air or a mixture of air and nitrogen (lean air) into the circulatory evaporator from below, for example at rates of 0.1-1, preferably 0.2-0.8 and more preferably 0.3-0.7 m$^3$/m$^3$h, based on the volume of the reaction mixture.

The course of the esterification can be monitored by monitoring the amount of water carried out.

The reaction can be ended for example as soon as 90%, preferably at least 95% and more preferably at least 98% of the theoretically expected amount of water has been carried out.

After the esterification has ended, the acidic catalyst is destroyed or removed in a conventional manner. This is accomplished by neutralization, preferably with aqueous sodium hydroxide solution, in the case of homogeneous catalysts, such as sulfuric acid for example, and by filtration in the case of heterogeneous catalysts, such as acidic ion exchangers for example.

In a further embodiment, the reaction mixture after the transesterification has ended may be diluted with water to a concentration of for example 10-90% by weight, preferably 20-80% by weight, more preferably 20-60% by weight, even more preferably 30-50% by weight and especially about 40% by weight, for example in order that the viscosity may be reduced.

If necessary, the reaction mixture may be decolorized, for example by treatment with activated carbon or metal oxides, for example alumina, silica, magnesium oxide, zirconium oxide, boron oxide or mixtures thereof, in amounts for example of 0.1-50% by weight, preferably from 0.5% to 25% by weight, more preferably 1-10% by weight at temperatures of for example from 10 to 100° C., preferably from 20 to 80° C. and more preferably from 30 to 60° C.

This can be effected by adding the pulverulent or granular decolorizing agent to the reaction mixture and subsequent filtration or by passing the reaction mixture through a bed of the decolorizing agent in the form of any desired suitable moldings.

The decolorizing of the reaction mixture can be effected at any desired stage in the workup process, for example at the stage of the crude reaction mixture or after any neutralization or solvent removal.

Any solvent used for the esterification and now present in the reaction mixture can be substantially removed by distillation. Low boilers in the reaction mixture will be removed as well in the process. Low boilers are components having a boiling point below that of the target ester.

The distillative removal of the main amount of solvent is effected for example in a stirred tank with jacketed heating and/or internal heating coils under reduced pressure, for example at 20-700 mbar, preferably 30-500 mbar and more preferably 50-150 mbar, and 40-120° C.

It will be appreciated that the distillation can also be accomplished in a falling-film or thin-film evaporator. For this, the reaction mixture is recirculated, preferably two or more times, through the apparatus under reduced pressure, for example at 20-700 mbar, preferably 30-500 mbar and more preferably 50-150 mbar, and 40-120° C.

When water is used as a diluent, the solvent which may be present can be removed by azeotropic distillation. The distillate may, after condensation, be fed to a phase separation apparatus. The thus obtained organic phase may be removed from the system, while the aqueous phase can likewise be removed from the system or fed as a reflux into the distillation unit.

An inert gas, preferably an oxygen-containing gas, more preferably air or a mixture of air and nitrogen (lean air) may preferably be introduced into the distillation apparatus, for example 0.1-1 $m^3/m^3h$, preferably 0.2-0.8 $m^3/m^3h$ and more preferably 0.3-0.7 $m^3/m^3h$, based on the volume of the reaction mixture.

The level of (meth)acrylic acid in the residue after distillation is generally below 5% by weight, preferably in the range from 0.001 to 5% by weight and more preferably in the range from 0.01 to 3% by weight.

The removed solvent may be condensed and preferably reused.

If necessary, a solvent stripping operation can be carried out in addition to or in lieu of the distillation.

For this, the target ester, which still contains small amounts of (meth)acrylic acid and/or solvent, is heated to 50-90° C. and preferably 80-90° C. and the remaining amounts of solvent are removed with a suitable gas in a suitable apparatus. A vacuum can be applied in support, if desired.

Examples of useful apparatus include columns of conventional design which contain conventional internals, for example trays, dumped packing or structured packing, preferably dumped packing. Useful column internals include in principle all common internals, for example trays, arranged packing and/or random packing. Preferred trays include bubble-cap trays, sieve trays, valve trays, Thormann trays and/or dual-flow trays, while preferred dumped packings are those of rings, coils, saddles, Raschig, Intos or Pall rings, barrel or Intalox saddles, Top-Pak, etc or braids.

Another possibility here is a failing-film, thin-film or wiped-film evaporator, for example a Luwa, Rotafilm or Sambay evaporator, which may be splash-guarded with a demister for example.

Useful gases include gases which are inert under the stripping conditions, preferably oxygen-containing gases, more preferably air or mixtures of air and nitrogen (lean air) or water vapor, especially such gases which have been preheated to 50-100° C.

The stripping gas rate is for example in the range from 5 to 20, more preferably in the range from 10 to 20 and most preferably in the range from 10 to 15 $m^3/m^3$ h, based on the volume of the reaction mixture.

If necessary, the (meth)acrylic ester of the monoalkoxylated polyol may at any stage of the workup process, but preferably after low-boilers removal has taken place, be subjected to a filtration in order that precipitated traces of salts and any decolorizing agent present may be removed.

The (meth)acrylic esters of monoalkoxylated polyols and inventive aqueous solutions obtainable by the above process may be used as a free-radical crosslinker of water-absorbing hydrogels,
as a starting material for producing polymer dispersions,
as a starting material for producing polyacrylates (apart from hydrogels),
as a paint raw material or
as a cement additive.

Especially those inventive (meth)acrylic esters of monoalkoxylated polyols are useful as a free-radical crosslinker of water-absorbing hydrogels that have a solubility in distilled water at 25° C. of not less than 5% by weight, preferably not less than 10% by weight, more preferably not less than 20% by weight, even more preferably not less than 30% by weight and especially not less than 50% by weight.

Useful hydrophilic monomers for preparing the crosslinked swellable hydrogel-forming polymers include for example acids capable of addition polymerization, such as acrylic acid, methacrylic acid, ethacrylic acid, α-chloroacrylic acid, crotonic acid, maleic acid, maleic anhydride, vinylsulfonic acid, vinylphosphonic acid, maleic acid, maleic anhydride, fumaric acid, itaconic acid, citraconic acid, mesaconic acid, glutaconic acid, aconitic acid, allylsulfonic acid, sulfoethyl acrylate, sulfoethyl methacrylate, sulfopropyl acrylate, sulfopropyl methacrylate, 2-hydroxy-3-acryloyloxypropylsulfonic acid, 2-hydroxy-3-methacryloyloxypropylsulfonic acid, allylphosphonic acid, styrenesulfonic acid, 2-acrylamido-2-methylpropanesulfonic acid, 2-acrylamido-2-methylpropane-phosphonic acid and also their amides, hydroxyalkyl esters and amino- or ammonio-containing esters and amides. These monomers can be used alone or mixed with each other. Furthermore water-soluble N-vinylamides and also diallyldimethylammonium chloride.

Particularly preferred hydrophilic monomers are acrylic acid and methacrylic acid.

To optimize properties, it can be sensible to use additional monoethylenically unsaturated compounds which do not bear an acid group but are copolymerizable with the monomers bearing acid groups. Such compounds include for example the amides and nitriles of monoethylenically unsaturated carboxylic acids, for example acrylamide, methacrylamide and N-vinylformamide, N-vinylacetamide, N-methylvinylacetamide, acrylonitrile and methacrylonitrile. Examples of further suitable compounds are vinyl esters of saturated $C_1$- to $C_4$-carboxylic acids such as vinyl formate, vinyl acetate or vinyl propionate, alkyl vinyl ethers having at least two carbon atoms in the alkyl group, for example ethyl vinyl ether or butyl vinyl ether, esters of monoethylenically unsaturated $C_3$- to $C_6$-carboxylic acids, for example esters of monohydric $C_1$- to $C_{18}$-alcohols and acrylic acid, methacrylic acid or maleic acid, monoesters of maleic acid, for example methyl hydrogen maleate, N-vinyllactams such as N-vinylpyrrolidone or N-vinylcaprolactam, acrylic and methacrylic esters of alkoxylated monohydric saturated alcohols, for example of alcohols having from 10 to 25 carbon atoms which have been reacted with from 2 to 200 mol of ethylene oxide and/or propylene oxide per mole of alcohol, and also monoacrylic esters and monomethacrylic esters of polyethylene glycol or polypropylene glycol, the molar masses ($M_n$) of the polyalkylene glycols being up to 2000, for example. Further suitable monomers are styrene and alkyl-substituted styrenes such as ethylstyrene or tert-butylstyrene.

These monomers without acid groups may also be used in mixture with other monomers, for example mixtures of vinyl acetate and 2-hydroxyethyl acrylate in any proportion. These monomers without acid groups are added to the reaction mixture in amounts within the range from 0 to 50% by weight, preferably less than 20% by weight.

The crosslinked (co)polymers preferably consist of acid-functional monoethylenically unsaturated monomers which have optionally been converted into their alkali metal or ammonium salts before or after polymerization and of 0-40% by weight based on their total weight of monoethylenically unsaturated monomers which do not bear acid groups.

The production of (meth)acrylic acid (co)polymers, polyacrylic acids and superabsorbents has been extensively described before, see for example "Modern Superabsorbent Polymer Technology", F. L. Buchholz and A. T. Graham, Wiley-VCH, 1998, pages 69 to 117.

Preference is given to such hydrogels which are obtained by crosslinking addition polymerization or copolymerization of acid-functional monoethylenically unsaturated monomers or salts thereof.

In the postcrosslinking process, the starting polymer is treated with a postcrosslinker and preferably during or after the treatment postcrosslinked and dried by raising the temperature, the crosslinker preferably being included in an inert solvent. Inert solvents are solvents which substantially do not react either with the starting polymer or with the postcrosslinker. Preference is given to such solvents which do not react chemically with the starting polymer or with the postcrosslinker to an extent of more than 90%, preferably more than 95%, more preferably more than 99% and especially more than 99.5%.

Postcrosslinking and drying is preferably carried out at from 30 to 250° C., especially 50-200° C. and most preferably at from 100 to 180° C. The surface postcrosslinking solution is preferably applied by spraying the polymer in suitable spray mixers. After spraying, the polymer powder is thermally dried, and the crosslinking reaction can take place not only before but also during the drying operation. Preference is given to spraying a solution of the crosslinker in reaction mixers or mixing and drying ranges such as for example Lödige mixers, BEPEX mixers, NAUTA mixers, SHUGGI mixers or PROCESSALL. It is moreover also possible to use fluidized bed dryers.

The drying operation can take place in the mixer itself, by heating of the shell or by blowing in hot air. Also suitable is a downstream dryer such as for example a shelf dryer, a rotary tube oven or a heatable screw. But it is also possible to utilize an azeotropic distillation as drying technique, for example. The preferred residence time at this temperature in the reaction mixer or dryer is below 60 min and more preferably below 30 min.

Preference is given to the above processes wherein the starting polymer is a polymeric (meth)acrylic acid or a poly (meth)acrylate, especially a polymeric acrylic acid or a polyacrylate obtained by free-radical polymerization using a polyfunctional ethylenically unsaturated free-radical crosslinker.

Preference is given to such processes wherein the free-radical crosslinker is used in a dose of 0.01-5.0% by weight, preferably 0.02-3.0% by weight, more preferably 0.03-2.5% by weight, especially 0.05-1.0% and specifically from 0.1% to 0.75% by weight based on the starting polymer.

The present invention also provides polymers prepared by one of the processes mentioned above and for their use in hygiene articles, packaging materials and nonwovens and also for the use of an abovementioned composition of matter for producing crosslinked or thermally crosslinkable polymers, especially in paints and varnishes.

The crosslinked swellable hydrogel-forming polymers to be used (starting polymers) are in particular polymers of (co)polymerized hydrophilic monomers, graft (co)polymers of one or more hydrophilic monomers on a suitable grafting base, crosslinked cellulose or starch ethers or natural products capable of swelling in aqueous fluids, for example guar derivatives. These hydrogels are known to one skilled in the art and are described for example in U.S. Pat. No. 4,28,082, DE-C-27 06 135, U.S. Pat. No. 4,340,706, DE-C-37 13 601, DE-C-28 40 010, DE-A-43 44 548, DE-A-40 20 780, DE-A-40 15 085, DE-A-39 17 846, DE-A-38 07 289, DE-A-35 33 337, DE-A-35 03 458, DE-A-42 44 548, DE-A-42 19 607, DE-A-40 21 847, DE-A-38 31 261, DE-A-35 11 086, DE-A-31 18 172, DE-A-30 28 043, DE-A-44 18 881, EP-A-0 801 483, EP-A-0 455 985, EP-A-0 467 073, EP-A-0 312 952, EP-A-0 205 874, EP-A-0 499 774, DE-A 26 12 846, DE-A-40 20 780, EP-A-0 205 674, U.S. Pat. No. 5,145,906, EP-A-0 530 438, EP-A-0 670 073, U.S. Pat. Nos. 4,057,521, 4,062, 817, 4,525,527, 4,295,987, 5,011,892, 4,076,663 or 4,931, 497. Also of particular suitability are crosslinked swellable hydrogel-forming polymers from a manufacturing operation as described in WO 01/38402 and also crosslinked swellable inorganic/organic hybrid hydrogel-forming polymers as described in DE 198 54 575. The content of the aforementioned patent documents, especially the hydrogels produced by the processes, is explicitly incorporated herein by reference.

Suitable grafting bases for crosslinked swellable hydrogel-forming polymers obtainable by graft copolymerization of olefinically unsaturated acids can be of natural or synthetic origin. Examples are starch, cellulose, cellulose derivatives and also other polysaccharides and oligosaccharides, polyalkylene oxides, especially polyethylene oxides and polypropylene oxides, and also hydrophilic polyesters.

The crosslinked swellable hydrogel-forming polymer is obtainable by free-radical graft copolymerization of acrylic acid or acrylate onto a water-soluble polymer matrix. Non-limiting examples of suitable water-soluble polymer matrices are alginates, polyvinyl alcohol and polysaccharides such as starch for example. A graft copolymerization for the purposes of the present invention utilizes a polyfunctional ethylenically unsaturated free-radical crosslinker.

The crosslinked swellable hydrogel-forming polymer can be an organic/inorganic hybrid polymer formed from a polymeric acrylic acid or polyacrylate on the one hand and a silicate, aluminate or aluminosilicate on the other. More particularly, the polymeric acrylic acid or polyacrylate used may have been obtained by free-radical polymerization using a polyfunctional ethylenically unsaturated free-radical crosslinker and formed using a water-soluble silicate or soluble aluminate or mixture thereof.

Preferred crosslinked swellable hydrogel-forming polymers are in particular polyacrylates, polymethacrylates and also the graft polymers described in U.S. Pat. Nos. 4,931,497, 5,011,892 and 5,041,496. Very particularly preferred crosslinked swellable hydrogel-forming polymers are the kneader polymers described in WO 01/38402 and the polyacrylate-based crosslinked swellable organic/inorganic hybrid hydrogel-forming polymers described in DE-A-1 98 545 75.

The substances prepared according to the present invention, which are useful as free-radical crosslinkers in crosslinked swellable hydrogel-forming polymers, can be used alone or in combination with other crosslinkers, for example internal or surface crosslinkers, for example the following:

Methylenebisacrylamide, methylenebismethacrylamide, esters of unsaturated mono- or polycarboxylic acids with polyols, such as diacrylate or triacrylate, for example butanediol diacrylate, butanediol dimethacrylate, ethylene glycol diacrylate, ethylene glycol dimethacrylate, and also trimethylolpropane triacrylate and allyl compounds such as allyl (meth)acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP-A-0 343 427. Further suitable cocrosslinkers are pentaerythritol triallyl ether, pentaerythritol tetraallyl ether, polyethylene glycol diallyl ether, monoethylene glycol diallyl ether, glycerol diallyl ether, glycerol triallyl ether, polyallyl ethers based on sorbitol and also ethoxylated variants thereof. Particularly preferred cocrosslinkers further include polyethylene glycol diacrylates, ethoxylated derivatives of trimethylolpropane triacrylate, for example Sartomer® SR 9035, and also ethoxylated derivatives of glycerol diacrylate and glycerol triacrylate. It is obviously also possible to use mixtures of the above crosslinkers.

Very particular preference is given to those crosslinked swellable hydrogel-forming polymers which are prepared using an inventively prepared (meth)acrylic ester of a monoalkoxylated polyols as sole free-radical crosslinker.

The crosslinked swellable hydrogen-forming polymer is preferably a polymeric acrylic acid or a polyacrylate.

The crosslinked swellable hydrogel-forming polymers are preparable by addition polymerization processes known per se. Preference is given to the addition polymerization in aqueous solution conducted as a gel polymerization. It involves, as stated above, dilute, preferably aqueous and more preferably 15-50% by weight aqueous, solutions of one or more hydrophilic monomers and optionally of a suitable grafting base being polymerized in the presence of a free-radical initiator by utilizing the Trommsdorff-Norrish effect (Makromol. Chem. 1, 169 (1947)) preferably without mechanical mixing. The polymerization reaction may be carried out at from 0° C. to 150° C., and preferably at from 10° C. to 100° C., not only at atmospheric pressure but also at superatmospheric or reduced pressure. Typically, the polymerization can also be carried out in a protective gas atmosphere, preferably under nitrogen. The addition polymerization may be induced using high-energy electromagnetic rays or the customary chemical polymerization initiators, for example organic peroxides, such as benzoyl peroxide, tert-butyl hydroperoxide, methyl ethyl ketone peroxide, cumene hydroperoxide, azo compounds such as azobisisobutyronitrile and also inorganic peroxy compounds such as $(NH_4)_2S_2O_8$, $K_2S_2O_8$ or $H_2O_2$.

They can if desired be used in combination with reducing agents such as ascorbic acid, sodium hydrogensulfite and iron(II) sulfate or redox systems where the reducing component included is an aliphatic and aromatic sulfinic acid, such as benzenesulfinic acid and toluenesulfinic acid or derivatives thereof, for example Mannich adducts of sulfinic acids, aldehydes and amino compounds, as described in DE-C-1 301 566. The performance properties of the polymers can be further improved by postheating the polymer gels in the temperature range from 50° C. to 130° C. and preferably from 70° C. to 100° C. for several hours.

The gels obtained are neutralized to the extent of 0-100 mol %, preferably 25-100 mol % and more preferably 50-85 mol % based on monomer used, for which the customary neutralizing agents can be used, preferably alkali metal hydroxides, alkali metal oxides or the corresponding alkali metal carbonates, but more preferably sodium hydroxide, sodium carbonate and sodium bicarbonate.

Neutralization is typically achieved by mixing the neutralizing agent as an aqueous solution or else preferably as a solid into the gel. For this, the gel is mechanically comminuted, for example by means of a meat grinder, and the neutralizing agent is sprayed on, scattered on or poured on and then carefully mixed in. The gel mass obtained can then be repeatedly passed through the meat grinder for homogenization. The neutralized gel mass is then dried with a belt or can dryer until the residual moisture content is preferably below 10% by weight and especially below 5% by weight.

The addition polymerization as such can also be carried out by any other process described in the literature. More particularly, the neutralization of the acrylic acid can also be carried out prior to the polymerization, as described above. The polymerization can then be carried out in a conventional belt reactor or a kneading reactor continuously or else batchwise. When the polymerization is carried out in a belt reactor, initiation by electromagnetic radiation and preferably by UV radiation or alternatively initiation by means of a redox initiator system is particularly preferred. Very particular preference is also given to a combination of the two methods of initiation: electromagnetic radiation and chemical redox initiator system simultaneously.

The dried crosslinked swellable hydrogel-forming polymer can then be ground and sieved, in which case it is customary to use roll mills, pin mills or vibratory mills for the grinding. The preferred particle size of the sieved hydrogel is preferably in the range 45-1000 µm, more preferably at 45-850 µm, even more preferably at 200-850 µm, and most preferably at 300-850 µm. These ranges preferably cover 80% by weight of the particles and especially 90% by weight of the particles. The size distribution can be determined using established laser methods.

The present invention further provides crosslinked swellable hydrogel-forming polymers which contain at least one hydrophilic monomer in polymerized form and are crosslinked with a (meth)acrylic ester of a monoalkoxylated polyol of the formula (I).

Preferred (meth)acrylic esters of monoalkoxylated polyols are those of the formula (I), as defined above.

The monoalkoxylated polyols which are described by the formula (II) and whose (meth)acrylic esters are used as a crosslinker in the aforementioned crosslinked swellable hydrogel-forming polymers are each alkoxylated, preferably ethoxylated, propoxylated or mixedly ethoxylated and propoxylated and especially ethoxylated or mixedly ethoxylated and propoxylated and most preferably exclusively ethoxylated.

Particularly preferred (meth)acrylic esters of monoalkoxylated polyols are those of the formula (I) whose monoalkoxylated polyols are derived from isopropylideneglycerol and isopropylidenetrimethylolpropane.

The CRC value [g/g] of the inventive crosslinked swellable hydrogel-forming polymers may be measured by the methods indicated in the description and is preferably above 15, especially above 20, more preferably above 25, especially above 30, more preferably above 35.

The AUL 0.7 psi value [g/g] of the inventive crosslinked swellable hydrogel-forming polymers may be rmeasured by the methods indicated in the description and is after postcrosslinking preferably above 5, especially above 10, more preferably above 15, especially above 20 and even more preferably 25.

The present invention further relates to the use of the abovementioned hydrogel-forming polymers in hygiene articles comprising (A) a liquid-pervious topsheet
(B) a liquid-impervious backsheet
(C) a core positioned between (A) and (B) and comprising
  10-100% by weight of the crosslinked swellable hydrogel-forming polymer according to the present invention
  0-90% by weight of hydrophilic fiber material
  preferably 30-100% by weight of the crosslinked swellable hydrogel-forming polymer according to the present invention, 0-70% by weight of hydrophilic fiber material
  more preferably 50-100% by weight of the crosslinked swellable hydrogel-forming polymer according to the present invention, 0-50% by weight of hydrophilic fiber material
  especially preferably 70-1 00% by weight of the crosslinked swellable hydrogel-forming polymer according to the present invention, 0-30% by weight of hydrophilic fiber material
  most preferably 90-100% by weight of the crosslinked swellable hydrogel-forming polymer according to the present invention, 0-10% by weight of hydrophilic fiber material
(D) optionally a tissue layer positioned directly above and below said core (C), and
(E) optionally an acquisition layer positioned between (A) and (C).

Hygiene articles for the purposes of the present invention include, for example, not only incontinence pads and incontinence briefs for adults but also diapers for infants.

The liquid-pervious topsheet (A) is the layer which is in direct contact with the skin. Its material comprises customary synthetic or manufactured fibers or films of polyesters, polyolefins, rayon or natural fibers such as cotton. In the case of non-woven materials the fibers are generally joined together by binders such as polyacrylates. Preferred materials are polyesters, rayon and blends thereof, polyethylene and polypropylene. Examples of liquid-pervious layers are described in WO 99/57355, EP-A71 023 883.

The liquid-impervious layer (B) is generally a sheet of polyethylene or polypropylene.

The core (C) includes not only the crosslinked swellable hydrogel-forming polymer according to the present invention but also hydrophilic fiber material. By hydrophilic is meant that aqueous fluids spread quickly over the fiber. The fiber material is usually cellulose, modified cellulose, rayon, polyester such as polyethylene terephthalate. Particular preference is given to cellulose fibers such as pulp. The fibers generally have a diameter of 1-200 µm and preferably 10-100 µm, and also have a minimum length of 1 mm.

Diaper construction and shape is common knowledge and described for example in WO 95/26209 page 66 line 34 to page 69 line 11, DE-A-196 04 601, EP-A-0 316 518 and EP-A-0 202 127. Diapers and other hygiene articles are generally also described in WO 00/65084, especially at pages 6-15, WO 00/65348, especially at pages 4-17, WO 00/35502, especially pages 3-9, DE-A-197 37 434, WO 98/08439. Hygiene articles for feminine care are described in the following references. The inventive crosslinked swellable hydrogel-forming polymers capable of absorbing aqueous fluids can be used there. Feminine care references: WO 95/24173: Absorption Article for Controlling Odour, WO 91/11977: Body Fluid Odour Control, EP-A-0 389 023: Absorbent Sanitary Articles, WO 94/25077: Odour Control Material, WO 97/01317: Absorbent Hygienic Article, WO 99/18905, EP-A-0 834 297, U.S. Pat. Nos. 5,762,644, 5,895, 381, WO 98/57609, WO 00/65083, WO 00/69485, WO 00/69484, WO 00/69481, U.S. Pat. No. 6,123,693, EP-A-1 104 666, WO 01/24755, WO 01/00115, EP-A-0 105 373, WO 01/41692, EP-A-1 074 233. Tampons are described in the following references: WO 98/48753, WO 98/41179, WO 97/09022, WO 98/46182, WO 98/46181, WO 01/43679, WO 01/43680, WO 00/61052, EP-A-1 108 408, WO 01/33962, DE-A-100 20 662, WO 01/01910, WO 01/01908, WO 01/01909, WO 01/01906, WO 01/01905, WO 01/24729. Incontinence articles are described in the following references: Disposable Absorbent Article for Incontinent Individuals: EP-A-0 311 344 description pages 3-9; Disposable Absorbent Article: EP-A-0 850 623; Absorbent Article: WO 95/26207; Absorbent Article: EP-A-0 894 502; Dry Laid Fibrous Structure: EP-A-0 850 616; WO 98/22063; WO 97/49365; EP-A-0 903 134; EP-A-0 887 060; EP-A-0 887 059; EP-A-0 887 058; EP-A-0 887 057; EP-A-0 887 056; EP-A-0 931 530; WO 99/25284; WO 98/48753. Feminine care and incontinence articles are described in the following references: Catamenial Device: WO 93/22998 description pages 26-33; Absorbent Members for Body Fluids: WO 95/26209 description pages 36-69; Disposable Absorbent Article: WO 98/20916 description pages 13-24; Improved Composite Absorbent Structures: EP-A-0 306 262 description pages 3-14; Body Waste Absorbent Article: WO 99/45973. These references are hereby expressly incorporated herein.

The crosslinked swellable hydrogel-forming polymers according to the present invention are very useful as absorbents for water and aqueous fluids, so that they may be used with advantage as a water retainer in market gardening, as a filter aid and particularly as an absorbent component in hygiene articles such as diapers, tampons or sanitary napkins.

In addition to the above-described crosslinked swellable hydrogel-forming polymers, the absorbent composition of the present invention includes constructions which include crosslinked swellable hydrogel-forming polymers or to which they are fixed. Any construction is suitable that is capable of accommodating crosslinked swellable hydrogel-forming polymers and also of being integrated into the absorption layer. A multiplicity of such compositions is already known. A construction for installing the crosslinked swellable hydrogel-forming polymers can be for example a fiber matrix consisting of a cellulose fiber mixture (air-laid web, wet laid web) or synthetic polymer fibers (meltblown web, spunbonded web) or else of a fiber blend of cellulose fibers and synthetic fibers. Possible fiber materials are detailed in the chapter which follows. The air-laid web process is described for example in WO 98/28478. Furthermore, open-celled foams or the like may be used to install crosslinked swellable hydrogel-forming polymers.

Alternatively, such a construction can be the result of fusing two individual layers to form one or better a multiplicity of chambers which contain the crosslinked swellable hydrogel-forming polymers. Such a chamber system is described in detail in EP-A-0 615 736 page 7 lines 26 et seq.

In this case, at least one of the two layers should be water pervious. The second layer may either be water pervious or water impervious. The layer material used may be tissues or other fabric, closed or open-celled foams, perforated films, elastomers or fabrics composed of fiber material. When the absorbent composition consists of a construction of layers, the layer material should have a pore structure whose pore dimensions are small enough to retain the crosslinked swellable hydrogel-forming polymer particles. The above examples of the construction of the absorbent composition also include laminates composed of at least two layers between which the crosslinked swellable hydrogel-forming polymers are installed and fixed.

Generally it is possible to fix hydrogel particles within the absorbent core to improve dry and wet integrity. Dry and wet integrity describes the ability to install crosslinked swellable hydrogel-forming polymers into the absorbent composition in such a way that they withstand external forces not only in the wet but also in the dry state and highly swellable polymer does not dislocate or spill out. The forces referred to are especially mechanical stresses as occur in the course of moving about while wearing the hygiene article or else the weight pressure on the hygiene article in the case of incontinence especially. As to fixation, one skilled in the art knows a multiplicity of possibilities. Examples such as fixation by heat treatment, addition of adhesives, thermoplastics, binder materials are noted in WO 95/26209 page 37 line 36 to page 41 line 14. The cited passage is thus part of this invention. Methods for enhancing wet strength are also to be found in WO 00/36216.

Furthermore, the absorbent composition may comprise a base material, for example a polymer film on which the crosslinked swellable hydrogel-forming polymer particles are fixed. The fixing may be effected not only on one side but also on both sides. The base material can be water pervious or water impervious.

The above constructions of the absorbent composition incorporate the crosslinked swellable hydrogel-forming polymers at a weight fraction of from 10-100% by weight, preferably 30-100% by weight, more preferably 50-100% by weight, especially preferably 70-100% by weight, and most preferably 90-100% by weight, based on the total weight of the construction and of the crosslinked swellable hydrogel-forming polymers.

The structure of the present absorbent composition according to the invention may be based on various fiber materials, which are used as a fiber network or matrices. The present invention includes not only fibers of natural origin (modified or unmodified) but also synthetic fibers.

A detailed overview of examples of fibers which can be used in the present invention is given in WO 95/26209 page 28 line 9 to page 36 line 8. The cited passage is thus part of this invention.

Examples of cellulose fibers include cellulose fibers which are customarily used in absorption products, such as fluff pulp and cellulose of the cotton type. The materials (soft- or hardwoods), production processes such as chemical pulp, semi-chemical pulp, chemothermomechanical pulp (CTMP) and bleaching processes are not particularly restricted. For instance, natural cellulose fibers such as cotton, flax, silk, wool, jute, ethylcellulose and cellulose acetate are used.

Suitable synthetic fibers are produced from polyvinyl chloride, polyvinyl fluoride, polytetrafluoroethylene, polyvinylidene chloride, polyacrylic compounds such as ORLON®, polyvinyl acetate, polyethyl vinyl acetate, soluble or insoluble polyvinyl alcohol. Examples of synthetic fibers include thermoplastic polyolefin fibers, such as polyethylene fibers (PULPEX®), polypropylene fibers and polyethylene-polypropylene bicomponent fibers, polyester fibers, such as polyethylene terephthalate fibers (DACRON® or KODEL®), copolyesters, polyvinyl acetate, polyethyl vinyl acetate, polyvinyl chloride, polyvinylidene chloride, polyacrylics, polyamides, copolyamides, polystyrene and copolymers of the aforementioned polymers and also bicomponent fibers composed of polyethylene terephthalate-polyethylene-isophthalate copolymer, polyethyl vinyl acetate/polypropylene, polyethylene/polyester, polypropylene/polyester, copolyester/polyester, polyamide fibers (nylon), polyurethane fibers, polystyrene fibers and polyacrylonitrile fibers. Preference is given to polyolefin fibers, polyester fibers and their bicomponent fibers. Preference is further given to thermally adhesive bicomponent fibers composed of polyolefin of the core-sheath type and side-by-side type on account of their excellent dimensional stability following fluid absorption.

The synthetic fibers mentioned are preferably used in combination with thermoplastic fibers. In the course of the heat treatment, the latter migrate to some extent into the matrix of the fiber material present and so constitute bond sites and renewed stiffening elements on cooling. Additionally the addition of thermoplastic fibers means that there is an increase in the present pore dimensions after the heat treatment has taken place. This makes it possible, by continuous addition of thermoplastic fibers during the formation of the absorbent layer, to continuously increase the fraction of thermoplastic fibers in the direction of the topsheet, which results in a similarly continuous increase in the pore sizes. Thermoplastic fibers can be formed from a multiplicity of thermoplastic polymers which have a melting point of less than 190° C., preferably in the range from 75° C. to 175° C. These temperatures are too low for damage to the cellulose fibers to be likely.

Lengths and diameters of the above-described synthetic fibers are not particularly restricted, and generally any fiber from 1 to 200 mm in length and from 0.1 to 100 denier (gram per 9000 meters) in diameter may preferably be used. Preferred thermoplastic fibers are from 3 to 50 mm in length, particularly preferred thermoplastic fibers are from 6 to 12 mm in length. The preferred diameter for the thermoplastic fiber is in the range from 1.4 to 10 decitex, and the range from 1.7 to 3.3 decitex (gram per 10 000 meters) is particularly preferred. The form of the fiber may vary; examples include woven types, narrow cylindrical types, cut/chopped yarn types, staple fiber types and continuous filament fiber types.

The fibers in the absorbent composition of the present invention can be hydrophilic and/or hydrophobic. According to the definition of Robert F. Gould in the 1964 American Chemical Society publication "Contact angle, wettability and adhesion", a fiber is referred to as hydrophilic when the contact angle between the liquid and the fiber (or the fiber surface) is less than 90° or when the liquid tends to spread spontaneously on the same surface. The two processes are generally coexistent. Conversely, a fiber is termed hydrophobic when a contact angle of greater than 90° is formed and no spreading is observed.

Preference is given to using hydrophilic fiber material. Particular preference is given to using fiber material which is weakly hydrophilic on the body side and most hydrophilic in the region surrounding the crosslinked swellable hydrogel-forming polymers. In the manufacturing process, layers having different hydrophilicities are used to create a gradient which channels impinging fluid to the hydrogel, where it is ultimately absorbed.

Suitable hydrophilic fibers for use in the absorbent composition of the present invention include for example cellulose fibers, modified cellulose fibers, rayon, polyester fibers, for example polyethylene terephthalate (DACRON®), and hydrophilic nylon (HYDROFIL®). Suitable hydrophilic fibers may also be obtained by hydrophilicizing hydrophobic fibers, for example the treatment of thermoplastic fibers obtained from polyolefins (e.g. polyethylene or polypropylene, polyamides, polystyrenes, polyurethanes, etc.) with surfactants or silica. However, for cost reasons and reasons of availability, cellulosic fibers are preferred.

The crosslinked swellable hydrogel-forming polymer particles are embedded into the fiber material described. This can be done in various ways, for example by using the hydrogel material and the fibers together to create an absorbent layer in the form of a matrix, or by incorporating highly swellable hydrogels into fiber mixture layers, where they are ultimately fixed, whether by means of adhesive or lamination of the layers.

The fluid-acquiring and -distributing fiber matrix may comprise synthetic fiber or cellulosic fiber or a mixture of synthetic fiber and cellulosic fiber, in which case the mixing ratio may vary from (100 to 0) synthetic fiber: (0 to 100) cellulosic fiber. The cellulosic fibers used may additionally have been chemically stiffened to increase the dimensional stability of the hygiene article.

The chemical stiffening of cellulosic fibers may be provided in different ways. A first way of providing fiber stiffening is by adding suitable coatings to the fiber material. Such additives include for example polyamide-epichlorohydrin coatings (Kymener® 557 H, Hercules Inc., Wilmington, Del. USA), polyacrylamide coatings (described in U.S. Pat. No. 3,556,932 or as the Parez® 631 NC commercial product from American Cyanamid Co., Stamford, Conn. USA), melamine-formaldehyde coatings and polyethyleneimine coatings.

Cellulosic fibers may also be chemically stiffened by chemical reaction. For instance, suitable crosslinker substances may be added to effect crosslinking taking place within the fiber. Suitable crosslinker substances are typical substances used for crosslinking monomers including but not limited to $C_2$-$C_8$-dialdehydes, $C_2$-$C_8$-monoaldehydes having acid functionality and in particular $C_2$-$C_9$-polycarboxylic acids. Specific substances from this series are for example glutaraldehyde, glyoxal, glyoxylic acid, formaldehyde and citric acid. These substances react with at least two hydroxyl groups within any one cellulose chain or between two adjacent cellulose chains within any one cellulose fiber. The crosslinking causes a stiffening of the fibers, to which greater dimensional stability is imparted as a result of this treatment. In addition to their hydrophilic character, these fibers exhibit uniform combinations of stiffening and elasticity. This physical property makes it possible to retain the capillary structure even under simultaneous contact with fluid and compressive forces and to prevent premature collapse.

Chemically crosslinked cellulose fibers are known and described in WO 91/11162, U.S. Pat. Nos. 3,224,926, 3,440,135, 3,932,209, 4,035,147, 4,822,453, 4,888,093, 4,898,642 and 5,137,537. The chemical crosslinking imparts stiffening to the fiber material, which is ultimately reflected in improved dimensional stability for the hygiene article as a whole. The individual layers are joined together by methods known to one skilled in the art, for example intermelting by heat treatment, addition of hot-melt adhesives, latex binders, etc.

Examples of processes to obtain an absorbent composition comprising for example a base material to which crosslinked swellable hydrogel-forming polymers are fixed on one or both sides are known and included by the invention but not limited thereto.

Examples of processes to obtain an absorbent composition comprising for example a fiber material blend of synthetic fibers (a) and cellulose fibers (b) embedded in crosslinked swellable hydrogel-forming polymers (c), the blend ratio varying from (100 to 0) synthetic fiber: (0 to 100) cellulose fiber, include (1) a process where (a), (b) and (c) are mixed together at one and the same time, (2) a process where a mixture of (a) and (b) is mixed into (c), (3) a process where a mixture of (b) and (c) is mixed with (a), (4) a process where a mixture of (a) and (c) is mixed into (b), (5) a process where (b) and (c) are mixed and (a) is continuously metered in, (6) a process where (a) and (c) are mixed and (b) is continuously metered in, and (7) a process where (b) and (c) are mixed separately into (a). Of these examples, processes (1) and (5) are preferred. The apparatus used in this process is not particularly restricted and any customary apparatus known to one skilled in the art can be used.

The absorbent composition obtained in this way can optionally be subjected to a heat treatment, so that an absorption layer having excellent dimensional stability in the moist state is obtained. The heat treatment process is not particularly restricted. Examples include heat treatment by feeding hot air or infrared irradiation. The temperature of the heat treatment is in the range from 60° C. to 230° C., preferably from 100C to 200° C., more preferably from 100° C. to 180° C.

The duration of the heat treatment depends on the type of synthetic fiber, its amount and the hygiene article production rate. Generally the duration of the heat treatment is in the range from 0.5 second to 3 minutes, preferably from 1 second to 1 minute.

The absorbent composition is generally provided for example with a liquid-pervious topsheet and a liquid-impervious backsheet. Furthermore, leg cuffs and adhesive tabs are attached to finalize the hygiene article. The materials and types of pervious topsheet and impervious backsheet and of the leg cuffs and adhesive tabs are known to one skilled in the art and are not particularly restricted. Examples thereof may be found in WO 95/26209.

The present invention further provides hygiene articles comprising crosslinked swellable hydrogen-forming polymers which contain at least one hydrophilic monomer in polymerized form and are crosslinked with a (meth)acrylic ester of a monoalkoxylated polyol of the formula (I).

The examples which follow illustrate the process of the present invention.

EXAMPLES

Reported quantites are parts by weight, unless otherwise stated.

Example 1

87 g of isopropylidenetrimethylolpropane are placed with 2.4 g of KOH, 45% in water, as an initial charge in an autoclave and together dewatered at 80° C. and reduced pressure (about 20 mbar). 440 g of ethylene oxide are then added at 145-155° C. and allowed to react off at this temperature under elevated pressure. The reaction has ended when no further change in pressure is observed. The reaction mixture is then stirred for a further 30 min at about 150° C. After purging with inert gas and cooling down to 60° C., the catalyst is separated off by addition of sodium pyrophosphate and subsequent filtration.

Example 2

Example 1 is repeated using 66 g of isopropylideneglycerol.

Example 3

917 parts of approximately 20-tuply ethoxylated isopropylidenetrimethylolpropane (as per Example 1) are hydrolyzed with 150 parts of water and 5 parts of sulfuric acid and esterified with 216 parts of acrylic acid in 345 parts of methylcyclohexane. Assistant materials added are 3 parts of hydroquinone monomethyl ether, 1 part of triphenyl phosphite and 1 part of hypophosphorous acid. 29 parts of water are removed before the entrainer is removed by vacuum distillation. The product is purified using a K300 filter.

Example 4

Example 3 is repeated using 800 parts of an approximately 20-tuply ethoxylated isopropylideneglycerol (as per Example 2).

Comparative Example

A Petri dish made of glass and having a rim height of about 10 cm and a diameter of 18.5 cm is charged with a solution prepared in a separate vessel. The solution is composed of the following components: 440 g of water, 91.5 g of acrylic acid, 961.1 g of a 37.3% by weight sodium acrylate solution, 3.66 g of Sartomer® SR 9035 (approximately 15-tuply ethoxylated trimethylolpropane triacrylate from Sartomer), 0.256 g of sodium persulfate, 0.098 g of DAROCURE® 1173 and 0.049 g of IRGACURE® 651 (both photoinitiators from CIBA GEIGY). The glass dish is placed centrally underneath a UVASPOT L 400 T UV lamp (from Dr. Hönle GmbH) in a lighting box. The dish is positioned such that the distance between lamp and liquid surface is 20 cm, which provides a UVA irradiation intensity of about 30 mW/cm². The dish is irradiated under these conditions for about 12 minutes. An ensuing addition polymerization reaction (temperature rises to 80-90° C.) gives an approximately 5.5 cm thick gel cylinder, which is mechanically comminuted by means of a meat grinder, dried at 160° in a through circulation drying cabinet, ground using an ultracentrifugal mill. The 150-800 μm sieve fraction is then isolated.

Example 5

The comparative example is repeated using 4.43 parts of approximately 20-tuply monoethoxylated trimethylolpropane triacrylate (as per Example 3).

Example 6

The comparative example is repeated using 4.28 parts of approximately 20-tuply monoethoxylated glycerol triacrylate (as per Example 4).

Test Methods

To determine the quality of surface crosslinking, the dried hydrogel may be tested using the following test methods:

Centrifuge Retention Capacity (CRC)

This method measures the free swellability of the hydrogel in a teabag. 0.2000±0.0050 g of dried hydrogel (particle size fraction 106-850 μm) are weighed into a teabag 60×85 mm in size which is subsequently sealed. The teabag is placed for 30 minutes in an excess of 0.9% by weight sodium chloride solution (at least 0.83 l of sodium chloride solution/1 g of polymer powder). The teabag is then centrifuged for 3 minutes at 250 G. The amount of liquid retained by the hydrogel is determined by weighing back the centrifuged teabag.

Absorbency Under Load (AUL) 0.3 psi (2070 Pa)

The measuring cell for determining AUL 0.3 psi is a Plexiglass cylinder 60 mm in internal diameter and 50 mm in height. Adhesively attached to its underside is a stainless steel sieve bottom having a mesh size of 36 μm. The measuring cell further includes a plastic plate having a diameter of 59 mm and a weight which can be placed in the measuring cell together with the plastic plate. The plastic plate and the weight together weigh 576 g. AUL 0.3 psi is determined by determining the weight of the empty Plexiglass cylinder and of the plastic plate and recording it as $W_0$. 0.900±0.005 g of hydrogel-forming polymer (particle size distribution 150-800 μm) is then weighed into the Plexiglass cylinder and distributed very uniformly over the stainless steel sieve bottom. The plastic plate is then carefully placed in the Plexiglass cylinder, the entire unit is weighed and the weight is recorded as $W_a$. The weight is then placed on the plastic plate in the Plexiglass cylinder. A ceramic filter plate 120 mm in diameter and 0 in porosity is then placed in the middle of a Petri dish 120 mm in diameter and 30 mm in height and sufficient 0.9% by weight sodium chloride solution is introduced for the surface of the liquid to be level with the filter plate surface without the surface of the filter plate being wetted. A round filter paper 90 mm in diameter and <20 μm in pore size (S&S 589 Schwarzband from Schleicher & Schüll) is subsequently placed on the ceramic plate. The Plexiglass cylinder containing hydrogel-forming polymer is then placed with plastic plate and weight on top of the filter paper and left there for 60 minutes. At the end of this period, the complete unit is removed from the filter paper and the Petri dish and subsequently the weight is removed from the Plexiglass cylinder. The Plexiglass cylinder containing swollen hydrogel is weighed together with the plastic plate and the weight recorded as $W_b$.

AUL was calculated by the following equation:

$$AUL\ 0.3\ psi\ [g/g]=[W_b-W_a]/[W_a-W_0]$$

Extractables

The 16 h extractables value is determined similarly to the description in EP-A-0 811 636 at page 13 line 1 to line 19.

The properties obtained for the hydrogels are summarized in the table which follows:

|  | CRC [g/g] | AUL (0.3 psi) | Extractables [%] |
| --- | --- | --- | --- |
| Comparative example | 42.0 | 7.9 | 15.3 |
| Example 5 | 38.6 | 6.9 | 12.6 |
| Example 6 | 38.8 | 6.1 | 13.4 |

It will be readily apparent to any person skilled in the art that the inventive crosslinkers when used in the same amount in equimolar terms provide superior crosslinking, as is shown by the low extractables in particular.

We claim:

1. (Meth)acrylic esters of monoalkoxylated polyols of a general formula (I)

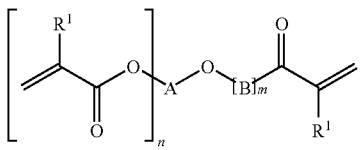

wherein
R$^1$ is hydrogen or methyl,
n is an integer from 2 to 5,
m is an integer from 1 to 100,
A is C$_3$ to C$_{20}$ alk(n+1)yl, and
B represents

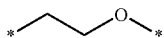

wherein * identifies positions of attachment.

2. (Meth)acrylic esters of monoalkoxylated polyols of claim 1 wherein
R$^1$ is hydrogen or methyl,
n is 2 or 3,
m is an integer from 2 to 50,
A is C$_3$ to C$_{10}$ alk(n+1)yl, and
B represents

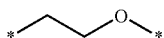

wherein * identifies the positions of attachment.

3. (Meth)acrylic esters of monoalkoxylated polyols of claim 1 wherein
R$^1$ is hydrogen or methyl,
n is 2,
m is an integer from 3 to 30,
A is C$_3$ to C$_6$ alk(n+1)yl, and
B is

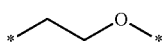

wherein * identifies the positions of attachment.

4. (Meth)acrylic esters of monoalkoxylated polyols of claim 1 wherein the polyol is glycerol.

5. A swellable hydrogel-forming polymer comprising a copolymerized (meth)acrylic ester of general formula (I)

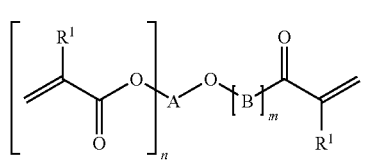

wherein
R$^1$ is hydrogen or methyl,
n is an integer from 2 to 5,
m is an integer from 1 to 100,
A is C$_3$ to C$_{20}$ alk(n+1)yl, and
B represents

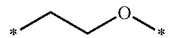

wherein * identifies positions of attachment as an internal crosslinker.

6. A process for preparing crosslinked swellable hydrogel-forming polymers which comprises polymerizing an aqueous mixture comprising a hydrophilic monomer, optionally at least one further monoethylenically unsaturated compound, at least one (meth)acrylic ester of a monoalkoxylated polyol of general formula (I)

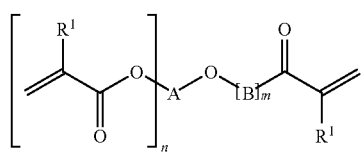

wherein
R$^1$ is hydrogen or methyl,
n is an integer from 2 to 5,
m is an integer from 1 to 100,
A is C$_3$ to C$_{20}$ alk(n+1)yl, and
B represents

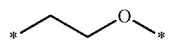

wherein * identifies positions of attachment, at least one free-radical initiator, optionally at least one grafting base, and optionally the hydrogel-forming polymer obtained being postcrosslinked, dried, and brought to a desired particle size.

7. A hygiene article comprising a crosslinked swellable hydrogel-forming polymer of claim 5.

8. (Meth)acrylic esters of monoalkoxylated polyols of claim 2 wherein the polyol is glycerol.

9. (Meth)acrylic esters of monoalkoxylated polyols of claim 3 wherein the polyol is glycerol.

10. A swellable hydrogel-forming polymer comprising a copolymerized (meth)acrylic ester of general formula (I) according to claim 2 as an internal crosslinker.

11. A swellable hydrogel-forming polymer comprising a copolymerized (meth)acrylic ester of general formula (I) according to claim 3 as an internal crosslinker.

12. A swellable hydrogel-forming polymer comprising a copolymerized (meth)acrylic ester of general formula (I) according to claim 4 as an internal crosslinker.

13. A hygiene article comprising a crosslinked swellable hydrogel-forming polymer of claim 10.

14. A hygiene article comprising a crosslinked swellable hydrogel-forming polymer of claim 11.

15. A hygiene article comprising a crosslinked swellable hydrogel-forming polymer of claim 12.

* * * * *